United States Patent [19]
Inoue et al.

[11] Patent Number: 5,969,186
[45] Date of Patent: Oct. 19, 1999

[54] PROCESS FOR RACEMIZING OF OPTICALLY ACTIVE AMINES

[75] Inventors: Toru Inoue; Yoshihiko Hirayama, both of Kobe, Japan

[73] Assignee: Nagase & Company, Ltd., Osaka, Japan

[21] Appl. No.: 09/155,516

[22] PCT Filed: Mar. 27, 1997

[86] PCT No.: PCT/JP97/01058

§ 371 Date: Sep. 25, 1998

§ 102(e) Date: Sep. 25, 1998

[87] PCT Pub. No.: WO97/35833

PCT Pub. Date: Oct. 2, 1997

[30] Foreign Application Priority Data

Mar. 28, 1996 [JP] Japan .................................. 8-073758

[51] Int. Cl.[6] .................................................. C07C 209/84
[52] U.S. Cl. ........................... 564/424; 564/381; 564/373
[58] Field of Search .................................. 564/424, 497, 564/381, 373

[56] References Cited

U.S. PATENT DOCUMENTS

| | | | |
|---|---|---|---|
| 3,970,700 | 7/1976 | Nagase et al. | 260/570.8 |
| 4,252,744 | 2/1981 | Bison et al. | 564/302 |
| 4,859,771 | 8/1989 | Reider et al. | 540/509 |
| 5,723,672 | 3/1998 | Nagata et al. | 564/424 |

FOREIGN PATENT DOCUMENTS

| | | | |
|---|---|---|---|
| 2348801 | 4/1975 | Germany | C07C 87/28 |
| 50-50328 | 5/1975 | Japan | C07B 20/0011 |
| 50-50344 | 5/1975 | Japan | C07C 87/4011 |
| 63-23824 | 2/1988 | Japan | C07B 57/00 |
| 63-185943 | 8/1988 | Japan | C07C 87/28 |
| 7-188120 | 7/1995 | Japan | C07C 211/29 |

*Primary Examiner*—Brian M. Burn
*Attorney, Agent, or Firm*—Jacobson, Price, Holman & Stern, PLLC

[57] ABSTRACT

The present invention provides a process for effectively racemizing an amine compound in which an asymmetric carbon is located at the β-position of the amino group or more distant therefrom, which comprises reacting the amine compound with a complex of an alkali metal and a polycyclic aromatic hydrocarbon.

9 Claims, No Drawings

PROCESS FOR RACEMIZING OF OPTICALLY ACTIVE AMINES

TECHNICAL FIELD

The present invention relates to a process for racemizing optically active amines of the formula (1) below which comprises reacting said optically active amine with a complex of an alkali metal and a polycyclic aromatic hydrocarbon.

BACKGROUND ART

Useful as optical resolution agents, as asymmetric auxiliary agents, as ligands for metals in an asymmetric reaction, or as intermediates for pharmaceuticals are optically active amines of the following formula (1):

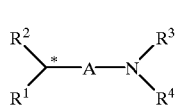
(1)

wherein
- $R^1$ is an unsubstituted aryl group; an aryl group substituted with one to five substituents selected from the group consisting of $C_1$–$C_4$ alkyl groups, $C_1$–$C_4$ alkoxy groups and halogen atoms; or an unsubstituted or substituted heterocyclic group;
- $R^2$ is a $C_1$–$C_8$ alkyl group; a $C_1$–$C_8$ alkyl group substituted with one to three aryl groups; a $C_1$–$C_8$ alkoxy group; a $C_1$–$C_8$ alkoxy group substituted with one to three aryl groups; an unsubstituted aryloxy group; an aryloxy group substituted with one to five substituents selected from the group consisting of halogen atoms, $C_1$–$C_4$ alkyl groups optionally substituted with one to three halogen atoms and $C_1$–$C_4$ alkoxy groups optionally substituted with one to three halogen atoms; or an unsubstituted aryl group; an aryl group substituted with one to five substituents selected from the group consisting of $C_1$–$C_4$ alkyl groups, $C_1$–$C_4$ alkoxy groups and halogen atoms; or an unsubstituted or substituted heterocyclic group; provided that these unsubstituted and substituted aryl and heterocyclic groups are not identical to $R^1$;
- $R^3$ and $R^4$, which may be identical or different, are chosen from hydrogen atoms, $C_1$–$C_4$ alkyl groups, $C_1$–$C_4$ alkyl groups substituted with one to three aryl groups, or $C_1$–$C_4$ alkyl-CO-groups;
- A is a $C_1$–$C_{10}$ alkylene group; and
- * indicates the position of the asymmetric carbon atom.

In particular, the optically active amine of the formula (1) wherein $R^1$ is phenyl, $R^2$ is isopropyl, $R^3$ and $R^4$ are both hydrogen atoms, and A is methylene, i.e., optically active 3-methyl-2-phenylbutylamine (PBA) is a useful compound as an optical resolution agent. The compound is used as an optical resolution agent for obtaining only one optically active isomer from racemic ibuprofen [2-(4-isobutylphenyl)propionic acid], ketoprofen [2-(3-benzoylphenyl)propionic acid] or the like, the isomer being useful as an anti-inflammatory, analgesic, antipyretic or antirheumatic agent [Japanese Patent Publication (Kokai) Nos. 229986/1993 and 151344/1996].

At present, optically active PBA can be obtained by resolving racemic PBA with an optically active acid such as mandelic acid [Japanese Patent Publication (Kokai) No. 172853/1986] or by selectively hydrolyzing an amide of PBA with an enzyme [Japanese Patent Application No. 215722/1995]. A method utilizing a reaction in which a nitrile undergoes optically selective hydration catalyzed by an enzyme has also been developed [Japanese Patent Publication (Kokai) No. 303496/1995].

If an optically active compound having either one of the steric configurations is desired and if one intends to obtain the optically active compound by optical resolution of its racemate, in general, the desired optically active compound is obtained only in 50% yield even at maximum, and not less than 50% of undesired optically active compound is discarded. Accordingly, if one intends to obtain an optically active compound by an optical resolution process, it is important to develop a process for racemization and/or inversion of the steric configuration of the undesired optically active compound so as to increase the yield of the desired optically active compound.

A number of processes for racemizing an amine compound in which a carbon atom at the α-position of the amino group is an asymmetric one have been developed, including, amongst others, a process of heating the amine compound under an atmosphere of pressurized hydrogen with a catalyst for catalytic reduction such as Raney nickel, Raney cobalt or the like [Japanese Patent Publication (Kokai) No. 185943/1988], a process utilizing an imine formed by a reaction of the amine compound with a carbonyl compound [Japanese Patent Publication (Kokai) Nos. 23824/1988 and 188120/1995], a process utilizing sodium hydride or sodium amide [DE-OS 2,348,801], and a process utilizing sodium activated by a polycyclic aromatic compound or by a carrier such as alumina [Japanese Patent Publication (Kokai) Nos. 50328/1975, 50344/1975 and 49235/1975].

However, up to now, no process has been known for effectively racemizing an amine compound in which an asymmetric carbon is located at the β-position of the amino group or more distant therefrom, as illustrated by PBA.

In view of these facts, the present inventors intended to develop an industrially applicable process for effectively racemizing an amine compound in which an asymmetric carbon is located at the β-position of the amino group or more distant therefrom, as illustrated by PBA.

DISCLOSURE OF THE INVENTION

Surprisingly, it was found that an amine compound in which an asymmetric carbon is located at the β-position of the amino group or more distant therefrom can be effectively racemized by reacting it with a complex of an alkali metal and a polycyclic aromatic hydrocarbon.

Thus, the present invention provides a process for racemizing optically active amines of the following formula (1):

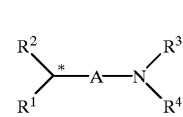
(1)

wherein
- $R^1$ is an unsubstituted aryl group; an aryl group substituted with one to five substituents selected from the group consisting of $C_1$–$C_4$ alkyl groups, $C_1$–$C_4$ alkoxy groups and halogen atoms; or an unsubstituted or substituted heterocyclic group;
- $R^2$ is a $C_1$–$C_8$ alkyl group; a $C_1$–$C_8$ alkyl group substituted with one to three aryl groups; a $C_1$–$C_8$ alkoxy group; a $C_1$–$C_8$ alkoxy group substituted with one to three aryl groups; an unsubstituted aryloxy group; an aryloxy group substituted with one to five substituents selected from the group consisting of halogen atoms, $C_1$–$C_4$ alkyl groups optionally substituted with one to three halogen atoms and $C_1$–$C_4$ alkoxy groups optionally substituted with one to three halogen atoms; or an unsubstituted aryl group; an aryl group substituted with one to five substituents selected from the group consisting of $C_1$–$C_4$ alkyl groups, $C_1$–$C_4$ alkoxy groups and halogen atoms; or an unsubstituted or substituted heterocyclic group; provided that these unsubstituted and substituted aryl and heterocyclic groups are not identical to $R^1$;

$R^3$ and $R^4$, which maybe identical or different, are chosen from hydrogen atoms, $C_1$–$C_4$ alkyl groups, $C_1$–$C_4$ alkyl groups substituted with one to three aryl groups, or $C_1$–$C_4$ alkyl-CO-groups;

A is a $C_1$–$C_{10}$ alkylene group; and

* indicates the position of the asymmetric carbon atom; which comprises reacting said amines with a complex of an alkali metal and a polycyclic aromatic hydrocarbon.

Base-induced racemization usually requires hydrogen atom abstraction reaction at the asymmetric carbon. Accordingly, such racemization becomes more prone to take place as the acidity of the hydrogen atom increases which is bound to the asymmetric carbon. However, the acidity of the hydrogen atom at the β-position of the amino group or more distant therefrom tends to become lower than the one at the α-position due to the attenuation in the inductive effect caused by the amino group. Therefore, it could not be assumed that a process which can effectively racemize an amine compound having an asymmetric carbon atom at the α-position of the amino group would be applicable to an amine compound in which an asymmetric carbon atom is located at the β-position of the amino group or more distant therefrom, as well.

As stated above, several processes for racemizing an amine compound in which an asymmetric carbon atom is located at the α-position of the amino group are known. These processes include a one which utilizes a complex of an alkali metal (sodium) and a polycyclic aromatic hydrocarbon (naphthalene or anthracene) [Japanese Patent Publication (Kokai) No. 49235/1975]. However, there has been no case in which the process is applied to an amine compound in which an asymmetric carbon atom is located at the β-position of the amino group or more distant therefrom. Thus, it was predicted that, if the process was applied to such an amine compound, its effectiveness would decline in a similar manner as is the case where the sodium hydride or sodium amide mediated process was employed.

Under such circumstances, the present inventors have found that the process utilizing a complex of an alkali metal and a polycyclic aromatic hydrocarbon is superior to other racemization processes and particularly effective in racemizing an amine compound having an asymmetric carbon atom at the β-position of the amino group or more distant therefrom, and completed the present invention as claimed herein.

BEST MODE FOR PRACTICING THE INVENTION

Optically active amine compounds to which the process of the present invention can be applied are those of the above formula (1) having an asymmetric carbon atom at the β-position of the amino group or more distant therefrom.

In the present specification, "aryl group" means a monofunctional aromatic hydrocarbon group and includes, for example, phenyl, biphenylyl and naphthyl groups.

"$C_1$–$C_4$ Alkyl group" and "$C_1$–$C_8$ alkyl group" mean linear or branched alkyl groups containing one to four and one to eight carbon atoms, respectively. Accordingly, $C_1$–$C_4$ alkyl groups include, for example, methyl, ethyl, n-propyl, isopropyl, n-butyl and t-butyl groups, and $C_1$–$C_8$ alkyl groups include, for example, n-pentyl, neopentyl, n-hexyl and n-octyl groups along with the aforementioned $C_1$–$C_4$ alkyl groups.

"$C_1$–$C_4$ Alkoxy group" and "$C_1$–$C_8$ alkoxy group" mean alkoxy groups in which each alkyl moiety consists of linear or branched alkyl groups containing one to four and one to eight carbon atoms, respectively. Accordingly, $C_1$–$C_4$ alkoxy groups include, for example, methoxy, ethoxy, n-propoxy, isopropoxy, n-butoxy and t-butoxy groups, and $C_1$–$C_8$ alkoxy groups include, for example, n-pentyloxy, neopentyloxy, n-hexyloxy and n-octyloxy groups along with the aforementioned $C_1$–$C_4$ alkoxy groups.

"Halogen atom" means fluorine, chlorine, bromine, or iodine atoms.

"Aryl group substituted with one to five substituents selected from the group consisting of $C_1$–$C_4$ alkyl groups, $C_1$–$C_4$ alkoxy groups and halogen atoms" means the above-defined aryl group substituted with one to five of the above-defined $C_1$–$C_4$ alkyl groups, $C_1$–$C_4$ alkoxy groups and/or halogen atoms. If plural substituents are present, they may be selected from the same or different groups or halogen atoms. This type of substituted aryl group includes, for example, p-, m- or o-fluoro, p-, m- or o-chloro, p-, m- or o-bromo, p-, m- or o-methoxy, p-, m- or o-ethoxy, p-, m- or o-butoxy, p-, m- or o-methyl, p-, m- or o-ethyl, p-, m- or o-propyl, p-, m- or o-butyl, p-, m- or o-isobutylphenyl group, mesityl group, or pentafluorophenyl group.

"$C_1$–$C_4$ Alkyl group and $C_1$–$C_8$ alkyl group substituted with one to three aryl groups" means the above-defined $C_1$–$C_4$ alkyl group and $C_1$–$C_8$ alkyl group substituted with one to three of the above-defined aryl groups. This type of aryl-substituted alkyl group includes, for example, 1- or 2-phenylethyl, 2,2-diphenylethyl and 1,1,1-triphenylethyl groups.

"$C_1$–$C_4$ Alkoxy group and $C_1$–$C_8$ alkoxy group substituted with one to three aryl groups" means the above-defined $C_1$–$C_4$ alkoxy group and $C_1$–$C_8$ alkoxy group substituted with one to three of the above-defined aryl groups. This type of aryl-substituted alkoxy group includes, for example, benzyloxy, diphenylmethoxy and triphenylmethoxy groups.

"Aryloxy group" means the aryloxy group in which the aryl moiety is one of the above-defined aryl groups.

"$C_1$–$C_4$ Alkyl group optionally substituted with one to three halogen atoms" means the above-defined $C_1$–$C_4$ alkyl group optionally substituted with one to three of the above-defined halogen atoms. This type of halogen-substituted $C_1$–$C_4$ alkyl group includes, for example, chloromethyl, dibromomethyl, trifluoromethyl, 2-chloroethyl, 3-iodopropyl and 4-bromobutyl groups.

"$C_1$–$C_4$ Alkoxy group optionally substituted with one to three halogen atoms" means the above-defined $C_1$–$C_4$ alkoxy group optionally substituted with one to three of the above-defined halogen atoms. This type of halogen-substituted $C_1$–$C_4$ alkoxy group includes, for example, chloromethoxy, dibromomethoxy, trifluoromethoxy, 2-chloroethoxy, 3-iodopropoxy and 4-bromobutoxy groups.

"Aryloxy group substituted with one to five substituents selected from the group consisting of halogen atoms, $C_1$–$C_4$ alkyl groups optionally substituted with one to three halogen atoms and $C_1-C_4$ alkoxy groups optionally substituted with one to three halogen atoms" means the above-defined aryloxy group substituted with one to five of the above-defined halogen atoms, the above-defined $C_1-C_4$ alkyl groups optionally substituted with the above-defined halogen atoms and/or the above-defined $C_1-C_4$ alkoxy groups optionally substituted with the above-defined halogen atoms.

"$C_1-C_4$ Alkyl-CO-group" means an acyl group in which the above-defined $C_1-C_4$ alkyl group is bound to a carbonyl group, and includes, for example, acetyl, propionyl, butyryl, isobutyryl, valeryl and pivaloyl groups.

"$C_1-C_6$ Alkylene group" and "$C_1-C_{10}$ alkylene group" mean linear or branched alkylene groups containing one to six and one to ten carbon atoms, respectively, and include, for example, methylene, ethylene, propylene, butylene, 1- or 2-methylethylene, and 1,1-, 1,2- or 2,2-dimethylethylene groups.

Unsubstituted or substituted heterocyclic groups include, for example, furyl, thienyl, oxazolyl, thiazolyl, pyridyl, pyrimidinyl, N-alkyl pyrrolyl, imidazolyl and pyrazolyl groups.

Of the amine compounds of the above formula (1), there are favorable groups for applying the present process.

Thus, the present process is preferably used for racemizing optically active amines of the formula (1) wherein $R^1$ is an unsubstituted phenyl or naphthyl group; a phenyl or naphthyl group substituted with one to five substituents selected from the group consisting of $C_1-C_4$ alkyl groups, $C_1-C_4$ alkoxy groups and halogen atoms; or an unsubstituted heterocyclic group; $R^2$ is a $C_1-C_4$ alkyl group; a $C_1-C_4$ alkyl group substituted with one to three phenyl groups; a $C_1-C_4$ alkoxy group; a $C_1-C_4$ alkoxy group substituted with one to three phenyl groups; an unsubstituted phenoxy or naphthoxy group; a phenoxy or naphthoxy group substituted with a substituent selected from the group consisting of halogen atoms, $C_1-C_4$ alkyl groups optionally substituted with one to three halogen atoms and $C_1-C_4$ alkoxy groups optionally substituted with one to three halogen atoms; or an unsubstituted heterocyclic group; $R^3$ and $R^4$, which may be identical or different, are chosen from hydrogen atoms, $C_1-C_4$ alkyl groups, or $C_1-C_4$ alkyl groups substituted with one to three phenyl groups; and A is a $C_1-C_6$ alkylene group.

Also, the present process is preferably used for racemizing optically active amines of the formula (1) wherein $R^1$ is an unsubstituted phenyl group or a phenyl group substituted with one to five substituents selected from the group consisting of $C_1-C_4$ alkyl groups, $C_1-C_4$ alkoxy groups and halogen atoms; $R^1$ is a $C_1-C_4$ alkyl group, a $C_1-C_4$ alkyl group substituted with one to three phenyl groups, a $C_1-C_4$ alkoxy group, an unsubstituted phenoxy group, or a phenoxy group substituted with a substituent selected from the group consisting of halogen atoms, $C_1-C_4$ alkyl groups optionally substituted with one to three halogen atoms and $C_1-C_4$ alkoxy groups optionally substituted with one to three halogen atoms; $R^3$ and $R^4$, which may be identical or different, are chosen from hydrogen atoms or $C_1-C_4$ alkyl groups; and A is a methylene or ethylene group.

Furthermore, the present process is preferably used for racemizing optically active amines of the following formula (2):

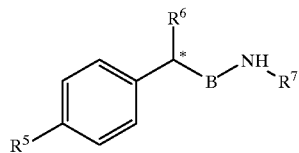

(2)

wherein $R^5$ is a hydrogen atom, a $C_1-C_4$ alkyl group, a $C_1-C_4$ alkoxy group or a halogen atom; $R^6$ is a $C_1-C_4$ alkyl group, a $C_1-C_4$ alkoxy group, an unsubstituted phenoxy group, or a phenoxy group substituted with a substituent selected from the group consisting of $C_1-C_4$ alkyl groups optionally substituted with one to three halogen atoms and $C_1-C_4$ alkoxy groups optionally substituted with one to three halogen atoms; $R^7$ is a hydrogen atom or a $C_1-C_4$ alkyl group; B is a methylene or ethylene group; and * indicates the position of the asymmetric carbon atom.

More preferably, the present process is used for racemizing optically active amines of the above formula (2) wherein $R^6$ is a $C_1-C_4$ alkyl group and B is a methylene group.

Also, the present process is preferably used for racemizing optically active amines of the above formula (2) wherein $R^6$ is a $C_1-C_4$ alkyl group, an unsubstituted phenoxy group, or a phenoxy group substituted with a methyl group optionally substituted with one to three halogen atoms and B is an ethylene group.

Most preferably, the present process is used for racemizing PBA, an optically active amine of the above formula (2) wherein $R^5$ is a hydrogen atom, $R^6$ is an isopropyl group, $R^7$ is a hydrogen atom, and B is a methylene group.

Racemic amine compounds of the above formula (1) or (2) are commercially available or can be obtained by known organic syntheses. Optically active amine compounds for racemizing according to the present process are frequently the residue obtained after optically resolving such racemic compounds and separating desired either one of optically active isomers. Accordingly, the optical purity of the optically active amine compounds used in the present process may be about 100% e.e. (enantiomer excess) or may be lower than this value, and may range from about 20 to 99% e.e.

Also, in the present process, racemization of optically active amines means that amines having a relatively high optical purity are converted into amines having a relatively low optical purity. Thus, according to the present process, optical purity of the aforementioned optically active amines can be reduced to 50% or below, preferably 20% or below, more preferably 10% or below, and most preferably 5% or below, relative to the optical purity of the starting amines.

The complex of an alkali metal and a polycyclic aromatic hydrocarbon used in the present process can be prepared from an alkali metal such as lithium, sodium or potassium and a polycyclic aromatic hydrocarbon such as naphthalene, alkylated naphthalene, anthracene, biphenyl, alkylated biphenyl or phenanthrene. Preferred complexes are those prepared from sodium and naphthalene, sodium and anthracene, or sodium and biphenyl.

The molar ratio of alkali metal to polycyclic aromatic hydrocarbon used is 50–0.5:1, preferably 20–0.7:1, and more preferably 10–0.9:1.

This type of complex can be easily prepared by mixing an alkali metal and a polycyclic aromatic hydrocarbon in an aprotic solvent such as toluene or THF or is commercially available. For example, there is a (1:1) sodium-naphthalene complex available from Kawaken Fine Chemicals Co., Ltd. Also, it is advantageous to prepare the complex for the present process such as sodium-naphthalene or sodium-anthracene complex by using the amine compound to be racemized as the solvent. Furthermore, the complex formation can be accelerated by sonicating a mixture of an alkali metal, polycyclic aromatic hydrocarbon and solvent, or by heating the mixture.

The present inventors have found that an alkali metal-polycyclic aromatic hydrocarbon complex can be prepared by using the amine compound to be racemized as a solvent and that it can also be prepared by sonicating or heating a mixture of the amine compound, an alkali metal and a polycyclic aromatic hydrocarbon. By doing so, the need to use a solvent such as THF can be omitted when preparing the complex. In addition, they found that there is no need to use an alkali metal and a polycyclic aromatic hydrocarbon in an equimolar amount and that the polycyclic aromatic hydrocarbon can be used in much less amounts compared to the alkali metal; the molar ratio of the alkali metal to the polycyclic aromatic hydrocarbon is in the range from 20:1 to 2:1. Thus, it is possible to reduce the amount of the polycyclic aromatic hydrocarbon, which must be removed after the reaction.

The amount of the complex may be catalytic against that of the amine compound to be racemized, with the molar ratio of the amine compound to the complex ranging from 1:1 to 200:1, preferably from 2:1 to 100:1, and more preferably from 3:1 to 20:1. To shorten the reaction time, a relatively large amount of the complex maybe used. Also, the complex maybe added in one portion at the beginning of the reaction, or it may be added in portions according to progress of the reaction.

The present racemizing reaction can be carried out without a solvent or in an aprotic solvent (toluene, THF, etc.) Racemization may be carried out by adding the amine compound to the complex of an alkali metal and a polycyclic aromatic hydrocarbon which has been prepared beforehand either in solvent or free of solvent, or by simultaneously mixing the alkali metal, polycyclic aromatic hydrocarbon and amine compound either in solvent or free of solvent.

Also, the present racemizing reaction is preferably carried out under an atmosphere of inert gas (nitrogen, argon, etc.).

Moreover, the present racemizing reaction is desirably carried out under anhydrous conditions. However, if an amine compound to be racemized contains some moisture, for example, the racemization can be accomplished by using the complex in an excess amount depending on the equivalent amount of water affecting the activity of the complex.

It has been found that the racemization can be accelerated by using one of the alkali metal halides such as KCl, KI and LiCl as an additive. Such an additive is added to the reaction system so that the molar ratio of the amine compound to the additive is in the range from 1:1 to 200:1, preferably from 2:1 to 100:1, and more preferably from 4:1 to 20:1.

The reaction temperature is normally in the range from −20 to 100° C., preferably from 0 to 70° C., and more preferably from 10 to 40° C. The reaction time is normally in the range from 1 to 100 hours and more conventionally from 3 to 30 hours, although it can vary depending on the reaction conditions such as the amount of complex added and the reaction temperature.

After the reaction, the reaction mixture is extracted with an organic solvent under acidic conditions to transfer the polycyclic aromatic hydrocarbon into an organic layer and the amine into an aqueous layer. The organic solvent employed is not limited to a particular one if it is immiscible with water; such solvent may be selected from toluene, hexane, ethers and esters. Then, the aqueous layer is alkalified with a base such as sodium hydroxide and extracted with such organic solvent as specified above to obtain the desired amine. Although the amine of sufficiently high purity can be obtained according to the above procedures, the amine of much higher purity may be obtained by carrying out distillation or the like, if necessary.

EXAMPLES

The present invention is illustrated more specifically based on the following examples, but it is not limited thereto.

In the examples, the optical purity of PBA is indicated by enantiomer excess (% e.e.), and determined by high performance liquid chromatography (HPLC) analysis under the following conditions:

Column: CROWNPAK CR (+) [Daicel] 0.4×15 cm;

Eluate: 0.1N $HClO_4$ aqueous solution/methanol=85/15;

Flow rate: 0.8 ml/min.;

Temperature: 40° C.;

Detection: UV 210 nm.

The titration yield of PBA is determined by titrating a solution of 500 mg of the post-reaction mixture in 30 ml of methanol with 0.1N hydrochloric acid in the presence of an indicator of phenolphthalein.

Example 1

Racemization of (S)-PBA with a sodium-naphthalene complex (S)-PBA of an optical purity of about 100% (10.64 g) and a sodium-naphthalene complex (the molar ratio of sodium/naphthalene=1/1) (0.95 g, 9.6 mol %) were mixed in a reaction vessel at room temperature (about 23 to 28° C.) under nitrogen atmosphere. After about 5 minutes, the mixture became a brown solution. The mixture was then stirred for 6 hours at room temperature. After adding methanol to terminate the reaction, hexane (30 ml), conc. hydrochloric acid (20 ml) and water (20 ml) were added to the mixture and extraction was carried out. The hexane layer was separated and the aqueous layer was alkalified by adding sodium hydroxide. Fresh hexane (30 ml) was added to the aqueous layer and extraction was carried out. The aqueous layer was extracted again with hexane (30 ml). After the hexane layers were combined and dried over anhydrous sodium sulfate, the mixture was filtrated and hexane was evaporated off. The residue was analyzed to reveal that PBA of an optical purity of 9.8% e.e. was obtained. The recovery rate of PBA was determined to be 88% by titration.

In a similar manner as described above, several reactions were carried out at various reaction temperatures. The results obtained are shown in Table 1.

TABLE 1

| Amount of complex (mol %) | Reaction temperature (°C.) | Reaction time (hrs) | Optical purity (% e.e.) | Percent recovery (%) |
| --- | --- | --- | --- | --- |
| 10.7 | 0 | 6.5 | 65.4 | 95 |
| 9.9 | 10 | 6 | 43.7 | 92 |

TABLE 1-continued

| Amount of complex (mol %) | Reaction temperature (°C.) | Reaction time (hrs) | Optical purity (% e.e.) | Percent recovery (%) |
|---|---|---|---|---|
| 9.6 | 28 | 6 | 9.8 | 88 |
| 9.8 | 40 | 6 | 29.7 | 81 |

From these results, it can be seen that the preferable reaction temperature is in the range from 10 to 40° C.

In the similar manner as described above, several reactions were carried out with various amounts of the complex. The results obtained are shown in Table 2.

TABLE 2

| Amount of complex (mol %) | Reaction temperature (°C.) | Reaction time (hrs) | Optical purity (% e.e.) | Percent recovery (%) |
|---|---|---|---|---|
| 2.0 | 26 | 6 | 60.5 | 93 |
| 5.1 | 26 | 28 | 24.3 | 88 |
| 9.6 | 28 | 6 | 9.8 | 88 |
| 19.2 | 26 | 12 | 3.0 | 92 |
| 50.0 | 26 | 2 | 59.5 | 93 |

From these results, it can be seen that the preferable equivalent ratio of (S)-PBA to the complex is in the range from 3:1 to 20:1.

Example 2

Racemization of (R)-PBA with a sodium-naphthalene complex

A mixture of (R)-PBA of an optical purity of 46.6% (85.43 g) and a sodium-naphthalene complex (7.80 g, 9.9 mol %) was stirred in a reaction vessel for 18 hours at room temperature under a nitrogen atmosphere. Then, the mixture was worked up in the same way as described in Example 1. After drying over sodium sulfate, purification by distillation provided 71.78 g of PBA (93–96° C./8 mmHg) in an optical purity of 4.2% e.e. The recovery of PBA was 84%.

Example 3

Racemization of (S)-PBA with a sodium-naphthalene complex in THF

A mixture of (S)-PBA of an optical purity of about 100% (10.43 g), a sodium-naphthalene complex (0.95 g, 9.8 mol %) and anhydrous THF (5 ml) was stirred in a reaction vessel for 6 hours at room temperature under a nitrogen atmosphere. Then, the reaction was quenched by adding methanol and the mixture was worked up. After drying over sodium sulfate, the volatile components were evaporated off to obtain 9.86 g of an oily substance. This was analyzed to reveal that PBA of an optical purity of 33.1% e.e. was obtained. The recovery of PBA was 95%.

Example 4

Racemization of (S)-PBA with a sodium-naphthalene complex in toluene

A mixture of (S)-PBA of an optical purity of about 100% (18.35 g), a sodium-naphthalene complex (1.66 g, 9.8 mol %) and toluene (2 ml) was stirred in a reaction vessel for 6 hours at room temperature under a nitrogen atmosphere. Then, the reaction was quenched by adding methanol and the mixture was worked up. After drying over sodium sulfate, the volatile components were evaporated off to obtain 18.60 g of an oily substance. This was analyzed to reveal that PBA of an optical purity of 25.1% e.e. was obtained. The recovery of PBA was 92%.

Example 5

Racemization of (S)-PBA with a sodium-naphthalene complex in the presence of KCl A mixture of (S)-PBA of an optical purity of about 100% (12.39 g), a sodium-naphthalene complex (1.12 g, 9.8 mol %) and potassium chloride (0.55 g, 9.8 mol %) was stirred in a reaction vessel for 6 hours at room temperature under a nitrogen atmosphere. Then, the reaction was quenched by adding methanol and the mixture was worked up. After drying over sodium sulfate, the volatile components were evaporated off to obtain 10.85 g of an oily substance. This was analyzed by HPLC to reveal that PBA of an optical purity of 6.5% e.e. was obtained. The recovery of PBA was 92%.

Example 6

Racemization of (S)-PBA with a sodium-naphthalene complex in the presence of KI (S)-PBA (12.47 g) was treated with a sodium-naphthalene complex (1.12 g, 9.7 mol %) under the same conditions as in Example 5 except for using potassium iodide (1.23 g, 9.7 mol %) instead of potassium chloride. As a result, 11.32 g of PBA of an optical purity of 8.1% e.e. was obtained. The recovery of PBA was 91%.

Example 7

Racemization of (S)-PBA with a sodium-naphthalene complex in the presence of LiCl The reaction was carried out under the same conditions as in Example 5, except that lithium chloride (0.31 g, 9.5 mol %), instead of potassium chloride, was added to a mixture of (S)-PBA (12.76 g) and a sodium-naphthalene complex (1.12 g, 9.5 mol %) As a result, 11.32 g of PBA of an optical purity of 10.1% e.e. was obtained. The recovery of PBA was 85%.

The results obtained from changing the kind of additives are summarized in Table 3.

TABLE 3

| | Amount of complex (mol %) | Additive (mol %) | Reaction time (hrs) | Optical purity (% e.e.) | Percent recovery (%) |
|---|---|---|---|---|---|
| Example 1 | 9.9 | none | 6 | 9.8 | 88 |
| Example 5 | 9.8 | KCl (9.8) | 6 | 6.5 | 92 |
| Example 6 | 9.7 | KI (9.7) | 6 | 8.1 | 91 |
| Example 7 | 9.5 | LiCl (9.5) | 6 | 10.1 | 85 |

From these results, it can be seen that the racemization can be accelerated by addition of an inorganic salt such as a potassium salt.

Example 8

Racemization of (S)-PBA with a sodium-naphthalene complex added in two portions

A mixture of (S)-PBA of an optical purity of about 100% (20.51 g) and a sodium-naphthalene complex (1.11 g, 5.8 mol %) was stirred in a reaction vessel at room temperature under a nitrogen atmosphere. After 5 hours, a portion of the reaction solution was taken and treated with methanol to quench the reaction. This was analyzed by HPLC to reveal that the optical purity was 20.3% e.e. A further amount of the sodium-naphthalene complex (0.93 g, 4.9 mol %) was added to the vessel and the mixture was stirred for additional 5 hours. The mixture was then worked up. After drying over sodium sulfate, the volatile components were evaporated off. Analysis of the residue revealed that PBA of an optical purity of 3.3% e.e. was obtained in a recovery of 89%.

Example 9

Racemization of (S)-PBA with a sodium-naphthalene complex added in two portions

A mixture of (S)-PBA of an optical purity of about 100%. (11.04 g) and a sodium-naphthalene complex (1.03 g, 10 mol %) was stirred in a reaction vessel at room temperature under a nitrogen atmosphere. After 5 hours, a further amount of the sodium-naphthalene complex (1.30 g, 12.7 mol %) was added to the vessel and the mixture was stirred for additional 23 hours. The mixture was then worked up. After drying over sodium sulfate, the volatile components were evaporated off. Analysis of the residue revealed that racemic PBA was obtained in a recovery of 79%.

Example 10

Racemization of (S)-PBA with a sodium-naphthalene complex in the presence of moisture A mixture of (S)-PBA of an optical purity of about 100% (8.56 g) containing 8.6 mol % of moisture and a sodium-naphthalene complex (0.80 g, 10.1 mol %) was stirred in a reaction vessel at room temperature under a nitrogen atmosphere. After 6 hours, a portion of the reaction solution was taken and treated with methanol to quench the reaction. This was analyzed by HPLC to reveal that the optical purity was 43.5% e.e. A further amount of the sodium-naphthalene complex (0.99 g, 12.5 mol %) was then added to the vessel and the mixture was stirred for additional 17 hours. The mixture was then worked up. After drying over sodium sulfate, the volatile components were evaporated off. Analysis of the residue revealed that PBA of an optical purity of 2.5% e.e. was obtained in a recovery of 85%.

Example 11

Racemization of (S)-PBA with a sodium-naphthalene complex under sonication (S)-PBA of an optical purity of about 100% (10.70 g), naphthalene (0.78 g, 9.3 mol %) and sodium (0.14 g, 9.3 mol %) were charged into a reaction vessel at room temperature under a nitrogen atmosphere. The sodium remained undissolved, no reaction taking place. The reaction vessel was immersed in a sonication washer and the sonication was applied for 6 minutes. During the sonication, the colorless, clear solution turned dark brown and the sodium completely dissolved after a short period of time. The mixture was then stirred for 6 hours at room temperature. A portion of the reaction solution was taken and treated with methanol to quench the reaction. This was analyzed by HPLC to reveal that the optical purity was 17.7% e.e. The reaction mixture was stirred for additional 16 hours and then worked up. After drying over sodium sulfate, the volatile components were evaporated off. Analysis of the residue revealed that PBA of an optical purity of 10.1% e.e. was obtained in a recovery of 90%.

Example 12

Racemization of (S)-PBA with a sodium-naphthalene complex under sonication (S)-PBA of an optical purity of about 100% (10.80 g), naphthalene (0.18 g, 2.1 mol %) and sodium (0.14 g, 9.3 mol %) were charged into a reaction vessel at room temperature under a nitrogen atmosphere. When sonication was applied for 5 minutes, the colorless, clear solution turned dark brown and the sodium completely dissolved after a short period of time. The mixture was then stirred for 6 hours at room temperature. A portion of the reaction solution was taken and treated with methanol to quench the reaction. This was analyzed by HPLC to reveal that the optical purity was 14.0% e.e. The reaction mixture was stirred for additional 16 hours and then worked up. As a result of analysis, it was found that PBA of an optical purity of 6.6% e.e. was obtained in a recovery of 87%.

Example 13

Racemization of (S)-PBA with a sodium-naphthalene complex under heating (S)-PBA of an optical purity of about 100% (10.25 g), naphthalene (0.78 g, 9.8 mol %) and sodium (0.14 g, 9.8 mol %) were charged into a reaction vessel at room temperature under a nitrogen atmosphere. After stirring with heating at 80° C. for 5 minutes, the colorless, clear solution turned dark brown and the sodium completely dissolved after a short period of time. After stirring at room temperature for 3 hours, the reaction was quenched by adding methanol and the mixture was then worked up. As a result of analysis, it was found that PBA of an optical purity of 41.8% e.e. was obtained in a recovery of 93%.

Example 14

Racemization of N-ethyl-PBA with a sodium-naphthalene complex

Optically active N-ethyl-PBA (4.34 g) and a sodium-naphthalene complex (0.69 g, 20 mol %) were allowed to react at room temperature under a nitrogen atmosphere for 5 hours. Then, the reaction was quenched by adding methanol and the mixture was worked up. The recovery of N-ethyl-PBA was determined to be 90% by titration. The specific rotation in methanol at 20° C. was $[\alpha]_D=-35.2$ for the starting substrate and −24.6 for that after reaction.

Example 15

Racemization of N-ethyl-PBA with a sodium-naphthalene complex added in two portions Optically active N-ethyl-PBA (10.0 g) and a sodium-naphthalene complex (1.33 g, 17 mol %) were allowed to react at room temperature under a nitrogen atmosphere for 6 hours. Then, sodium-naphthalene (0.94 g, 12 mol %) was further added and the mixture was stirred for additional 25 hours. The reaction was quenched by adding methanol and the mixture was worked up. The recovery of N-ethyl-PBA was determined to be 67% by titration. The specific rotation in methanol at 20° C. was $[\alpha]_D=-35.2$ for the starting substrate and −14.0 for that after reaction.

Example 16

Racemization of N-ethyl-PBA with a sodium-naphthalene complex added in three portions Optically active N-ethyl-PBA (9.58 g) and a sodium-naphthalene complex (0.79 g, 10 mol %) were allowed to react at room temperature under a nitrogen atmosphere for 24 hours. Then, a sodium-naphthalene complex (1.01 g, 13 mol %) was added and the mixture was stirred for additional 26 hours. Again, a sodium-naphthalene complex (0.78 g, 10 mol %) was added and the mixture was stirred for additional 22 hours. Then, the reaction was quenched by adding methanol and the mixture was worked up. The recovery of N-ethyl-PBA was 67%. Specific rotation in methanol at 20° C. was $[\alpha]_D$=−35.2 for the starting substrate and −8.34 for that after reaction.

Example 17

Racemization of (S)-PBA with a sodium-anthracene complex

A sodium-anthracene complex was prepared by stirring a mixture of anthracene (2.18 g), sodium (0.28 g) and THF (5 ml) in a reaction vessel at room temperature under a nitrogen atmosphere. After an hour, (S)-PBA of an optical purity of about 100% (9.92 g) was added to the mixture. The mixture was stirred for 19 hours and then worked up. After drying over sodium sulfate, the volatile components were evaporated off. Analysis of the residue revealed that PBA of an optical purity of 59.7% e.e. was obtained in a recovery of 91%.

Example 18

Racemization of (S)-PBA with a sodium-biphenyl complex

A mixture of THF (5 ml), biphenyl (1.89 g, 20 mol %) and sodium (0.28 g, 20 mol %) was stirred in a reaction vessel at room temperature under a nitrogen atmosphere. After an hour, the mixture became a blue-violet homogeneous solution. (S)-PBA of an optical purity of about 100% (9.92 g) was added to the solution. After 26 hours, the reaction was quenched by adding methanol and the mixture was worked up. After drying over sodium sulfate, the volatile components were evaporated off. Analysis of the residue revealed that PBA was obtained in a recovery of 81%. Sampling was carried out during the reaction and the optical purity was determined: 25.8% e.e. after 4 hours and 1.1% e.e. after 19 hours.

Example 19

Racemization of (S)-PBA with a sodium-biphenyl complex under sonication (S)-PBA of an optical purity of about 100% (10.59 g), biphenyl (0.94 g, 9.4 mol %) and sodium (0.14 g, 9.4 mol %) were charged into a reaction vessel at room temperature under a nitrogen atmosphere. The sodium remained undissolved, no reaction taking place. The reaction vessel was immersed in a sonication washer and sonication was applied for 8 minutes. During the sonication, the colorless, clear solution became light brown and the sodium completely dissolved after a short period of time. The mixture was then stirred for one day at room temperature. The reaction was quenched by adding methanol and the mixture was worked up. After drying over sodium sulfate, the volatile components were evaporated off. Analysis of the residue revealed that PBA of an optical purity of 3.7% e.e. was obtained in a recovery of 89%. Sampling was carried out during the reaction and the optical purity was determined: 43.1% e.e. after 3 hours and 11.0% e.e. after 19 hours.

Example 20

Racemization of 3-(4-isobutylphenyl)butylamine with a sodium-biphenyl complex

A mixture of THF (2 ml), biphenyl (0.38 g, 10 mol %) and sodium (0.06 g, 10 mol %) was stirred in a reaction vessel at room temperature under a nitrogen atmosphere. After an hour, the mixture became a blue-violet homogeneous solution. Optically active 3-(4-isobutylphenyl)butylamine (5.00 g) was added to the solution. After 24 hours, the reaction was quenched by adding methanol and the mixture was worked up. After drying over sodium sulfate, the volatile components were evaporated off. Analysis of the residue revealed that the recovery of 3-(p-isobutylphenyl)-butylamine was 89%. The specific rotation in methanol at 20° C. was $[\alpha]_D$=−20.16 for the starting substrate and 0 for the recovered amine. Thus, it was demonstrated that complete racemization was accomplished.

Example 21

Racemization of 3-methyl-2-(4-methylphenyl)butylamine (4-methyl-PBA) with a sodium-biphenyl complex A mixture of THF (4 ml), biphenyl (0.77 g, 9 mol %) and sodium (0.12 g, 9 mol %) was stirred in a reaction vessel at room temperature under a nitrogen atmosphere. After an hour, the mixture became a blue-violet homogeneous solution. 4-Methyl-PBA of an optical purity of 50% e.e. (10.00 g) was added to the solution. After 16 hours, the reaction was quenched by adding methanol and the mixture was worked up. After drying over sodium sulfate, the volatile components were evaporated off. Analysis of the residue revealed that the recovery of 4-methyl-PBA was 89% and its optical purity was 14% e.e.

Example 22

Racemization of 3-(p-trifluoro-methylphenoxy)-3-phenylpropylamine with a sodium-naphthalene complex A mixture of optically active 3-(p-trifluoromethylphenoxy)-3-phenylpropylamine (4.93 g) and a sodium-naphthalene complex (0.60 g) was stirred in a reaction vessel at room temperature under a nitrogen atmosphere. After 12 hours, the reaction was quenched by adding methanol and the mixture was worked up. After drying over sodium sulfate, the volatile components were evaporated off. Analysis of the residue revealed that the recovery of 3-(p-trifluoromethylphenoxy)-3-phenylpropylamine was almost quantitative. The specific rotation at 25° C. was $[\alpha]_D$ (c=2, in methanol)=0.99 for the starting substrate and 0.00 for the recovered amine. Thus, the racemization proceeded in a degree of 100%.

Example 23

Racemization of 3-(p-trifluoro-methylphenoxy)-3-phenylpropylamine with a sodium-biphenyl complex A mixture of THF (4 ml), biphenyl (0.62 g, 20 mol %) and sodium (0.09 g, 20 mol %) was stirred in a reaction vessel at room temperature under a nitrogen atmosphere. After an hour, the mixture became a blue-violet homogeneous solution. Optically active 3-(p-trifluoromethylphenoxy)-3-phenylpropylamine (5.91 g) was added to the solution. After 17 hours, the reaction was quenched by adding methanol and the mixture was worked up. After drying over sodium sulfate, the volatile components were evaporated off. Analysis of the residue revealed that the recovery of 3-(p-trifluoromethylphenoxy)-3-phenylpropylamine was almost quantitative. The specific rotation at 25° C. was $[\alpha]_D$ (c=2, in methanol)=0.99 for the starting substrate and 0.50 for the recovered amine. Thus, the racemization proceeded in a degree of 49.

INDUSTRIAL UTILIZATION

As described above, it is possible to effectively racemize optically active amines in which an asymmetric carbon is located at the β-position of the amino group or more distant therefrom (for example, optically active PBA) by using the present process. Thus, by combining the present process with an optical resolution process, it is possible to effectively produce a desired optically active amine having either one of the steric configurations.

We claim:

1. A process for racemizing an optically active amine of the following formula (1):

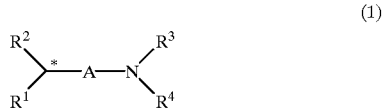

(1)

wherein $R^1$ is an unsubstituted aryl group; an aryl group substituted with one to five substituents selected from the group consisting of $C_1$–$C_4$ alkyl groups, $C_1$–$C_4$ alkoxy groups and halogen atoms; or an unsubstituted or substituted heterocyclic group;

$R^2$ is a $C_1$–$C_8$ alkyl group; a $C_1$–$C_8$ alkyl group substituted with one to three aryl groups; a $C_1$–$C_8$ alkoxy group; a $C_1$–$C_8$ alkoxy group substituted with one to three aryl groups; an unsubstituted aryloxy group; an aryloxy group substituted with one to five substituents selected from the group consisting of halogen atoms, $C_1$–$C_4$ alkyl groups optionally substituted with one to three halogen atoms and $C_1$–$C_4$ alkoxy groups optionally substituted with one to three halogen atoms; or an unsubstituted aryl group; an aryl group substituted with one to five substituents selected from the group consisting of $C_1$–$C_4$ alkyl groups, $C_1$–$C_4$ alkoxy groups and halogen atoms; or an unsubstituted or substituted heterocyclic group; provided that these unsubstituted and substituted aryl and heterocyclic groups are not identical to $R^1$;

$R^3$ and $R^4$, which may be identical or different, are chosen from hydrogen atoms, $C_1$–$C_4$ alkyl groups, $C_1$–$C_4$ alkyl groups substituted with one to three aryl groups, or $C_1$–$C_4$ alkyl-CO-groups;

A is a $C_1$–$C_{10}$ alkylene group; and

* indicates the position of the asymmetric carbon atom; which comprises reacting said amine with a complex of an alkali metal and a polycyclic aromatic hydrocarbon.

2. The process according to claim 1 in which the optically active amine of the formula (1) is racemized wherein $R^1$ is an unsubstituted phenyl or naphthyl group; a phenyl or naphthyl group substituted with one to five substituents selected from the group consisting of $C_1$–$C_4$ alkyl groups, $C_1$–$C_4$ alkoxy groups and halogen atoms; or an unsubstituted heterocyclic group; $R^2$ is a $C_1$–$C_4$ alkyl group; a $C_1$–$C_4$ alkyl group substituted with one to three phenyl groups; a $C_1$–$C_4$ alkoxy group; a $C_1$–$C_4$ alkoxy group substituted with one to three phenyl groups; an unsubstituted phenoxy or naphthoxy group; a phenoxy or naphthoxy group substituted with a substituent selected from the group consisting of halogen atoms, $C_1$–$C_4$ alkyl groups optionally substituted with one to three halogen atoms and $C_1$–$C_4$ alkoxy groups optionally substituted with one to three halogen atoms; or an unsubstituted heterocyclic group; $R^3$ and $R^4$, which may be identical or different, are chosen from hydrogen atoms, $C_1$–$C_4$ alkyl groups, or $C_1$–$C_4$ alkyl groups substituted with one to three phenyl groups; and A is a $C_1$–$C_6$ alkylene group.

3. The process according to claim 2 in which the optically active amine of the formula (1) is racemized wherein $R^1$ is an unsubstituted phenyl group or a phenyl group substituted with one to five substituents selected from the group consisting of $C_1$–$C_4$ alkyl groups, $C_1$–$C_4$ alkoxy groups and halogen atoms; $R^2$ is a $C_1$–$C_4$ alkyl group, a $C_1$–$C_4$ alkyl group substituted with one to three phenyl groups, a $C_1$–$C_4$ alkoxy group, an unsubstituted phenoxy group, or a phenoxy group substituted with a substituent selected from the group consisting of halogen atoms, $C_1$–$C_4$ alkyl groups optionally substituted with one to three halogen atoms and $C_1$–$C_4$ alkoxy groups optionally substituted with one to three halogen atoms; $R^3$ and $R^4$, which may be identical or different, are chosen from hydrogen atoms or $C_1$–$C_4$ alkyl groups; and A is a methylene or ethylene group.

4. The process according to claim 3 in which the optically active amine of the following formula (2) is racemized:

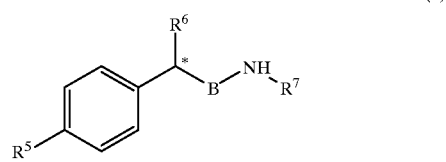

(2)

wherein $R^5$ is a hydrogen atom, a $C_1$–$C_4$ alkyl group, a $C_1$–$C_4$ alkoxy group or a halogen atom, $R^6$ is a $C_1$–$C_4$ alkyl group, a $C_1$–$C_4$ alkoxy group, an unsubstituted phenoxy group, or a phenoxy group substituted with a substituent selected from the group consisting of $C_1$–$C_4$ alkyl groups optionally substituted with one to three halogen atoms and $C_1$–$C_4$ alkoxy groups optionally substituted with one to three halogen atoms, $R^7$ is a hydrogen atom or a $C_1$–$C_4$ alkyl group, B is a methylene or ethylene group, and * indicates the position of the asymmetric carbon atom.

5. The process according to claim 4 in which the optically active amine of the formula (2) wherein $R^6$ is a $C_1$–$C_4$ alkyl group and B is a methylene group is racemized.

6. The process according to claim 4 in which the optically active amine of the formula (2) wherein $R^6$ is a $C_1$–$C_4$ alkyl group, an unsubstituted phenoxy group, or a phenoxy group substituted with a methyl group optionally substituted with one to three halogen atoms and B is an ethylene group is racemized.

7. The process according to claim 1 in which the complex of an alkali metal and a polycyclic aromatic hydrocarbon is a sodium-naphthalene, sodium-anthracene or sodium-biphenyl complex.

8. The process according to claim 7 in which a sodium-naphthalene, sodium-anthracene or sodium-biphenyl complex is prepared by using an optically active amine to be racemized as a solvent.

9. The process according to claim 8 in which a sodium-naphthalene, sodium-anthracene or sodium-biphenyl complex is prepared by sonicating or heating a mixture of an optically active amine to be racemized, sodium, and naphthalene, anthracene or biphenyl.

* * * * *